United States Patent
Kamis et al.

(10) Patent No.: US 6,656,457 B2
(45) Date of Patent: Dec. 2, 2003

(54) DUAL-PHASED STYLING PRODUCT THAT PROVIDES STYLING AND CONDITIONING BENEFITS

(75) Inventors: Kimberly Kamis, Solon, OH (US); Mark Dailey (II), Chicago, IL (US); Matthew Kuznitz, Buffalo Grove, IL (US); Keith Leslie Rutherford, Wirral Merseyside (GB); Robert George Riley, Chester (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 10/058,589

(22) Filed: Jan. 28, 2002

(65) Prior Publication Data

US 2002/0139384 A1 Oct. 3, 2002

Related U.S. Application Data

(60) Provisional application No. 60/265,386, filed on Jan. 30, 2001.

(51) Int. Cl.[7] .................................................. A61K 7/09
(52) U.S. Cl. .................. 424/70.2; 424/70.11; 424/70.12
(58) Field of Search ............................ 424/70.2, 70.12, 424/70.11

(56) References Cited

U.S. PATENT DOCUMENTS

| 5,059,414 A | 10/1991 | Dallal et al. |
| 5,756,106 A | 5/1998 | Concannon et al. |
| 5,968,495 A | 10/1999 | Bolich, Jr. et al. |

*Primary Examiner*—Jyothsna Venkat
(74) *Attorney, Agent, or Firm*—Milton L. Honig

(57) ABSTRACT

A hair styling and conditioning composition, for use in heat styling hair, and which are dual-phased until shaken, and wherein said composition comprises:

(a) a hydroalcoholic phase comprising at least one hair fixative; an emulsifier; a salt; and (b) an anhydrous phase comprising at least one volatile silicone or volatile hydrocarbon, are described. A method for heat styling hair so as to obtain both styling and conditioning benefits, which comprises applying a composition of the invention to hair prior to the application of heat, is also described.

7 Claims, No Drawings

DUAL-PHASED STYLING PRODUCT THAT PROVIDES STYLING AND CONDITIONING BENEFITS

CROSS REFERENCES

This application claims benefit of U.S. Provisional Application Ser. No. 60/265,386 filed Jan. 30, 2001.

BACKGROUND OF THE INVENTION

Using hair fixatives in hair styling products to afford hold and control benefits to hair is well known. Hair styling product is applied to hair which is then treated with heat through the use of a blow dryer or a curling iron, for example. This type of treatment has been termed heat styling.

Unfortunately, heat styling only affords the consumer, styling, control, and hold benefits. Hair which has only been stiffened by such treatment is not always desired by the consumer. It is an object of the present invention to provide a hair styling composition which can be used for the heat styling of hair, but which also conditions the hair after such heat styling.

It is another object of the present invention to provide a hair styling composition which can be used for the heat styling of hair, but which also provides a hair softening and a hair bodifying benefit.

The following patents and publications are related to the field of the invention.

U.S. Pat. No. 5,756,106 discloses a hair care composition for treatment of hair before heat styling comprising a discrete first composition having at least one moisture holding ingredient, an emulsifier, and an ingredient which is a salt that helps break the emulsion after use, and a discrete second composition having at least one lubricant.

U.S. Pat. No. 5,968,495 discloses relatively high VOC hair styling compositions which provide good style retention without unacceptable stickiness or stiffness. The compositions comprise from about 0.01% to about 20% of a hair styling polymer, and from about 0.5% to about 95% of a carrier comprising:

(i) from about 0.5% to 55% of the carrier of a first solvent selected form water, water soluble organic solvents, other organic solvents; and (ii) from about 40% to 95% by weight of the carrier of $C_1$–$C_3$ monohydric alcohols, ketones, ethers or mixtures thereof.

SUMMARY OF THE INVENTION

The invention relates to dual phase hair styling compositions which afford hair style, control and hold benefits, while at the same time providing hair conditioning, softening and bodifying benefits.

The hair styling compositions of the invention comprise dual-layers or phases which are shaken or mixed just prior to use to form a single-phase composition that is applied often to wet hair, which is then heated in a heat styling procedure. The composition returns to its dual-layer appearance an hour or more after use.

The first layer is a hydro-alcoholic layer containing hair fixatives in order to supply the desired hold and control and styling benefits. The second layer is anhydrous and comprises a volatile silicone such as a volatile cyclosiloxane like cyclomethicone; or a volatile linear dimethylsiloxane such as dimethicone. These silicones deliver conditioning benefits. The second layer may also be a volatile hydrocarbon.

Another aspect of the invention is to provide a hair styling and conditioning composition which affords, in storage, a pleasing dual-phased appearance.

Another aspect of the invention is to provide a method for styling and conditioning hair which comprises contacting said hair with a composition of the invention followed by applying heat to said hair with a heating appliance.

DETAILED DESCRIPTION OF THE INVENTION

Unless indicated otherwise, as used herein, % means weight %. As used herein the term "volatile" refers to materials that are liquid under ambient conditions and have a vapor pressure as measured at 25° C. of at least about 0.01 mm Hg, typically from about 0.01 mm Hg to 6.0 mm Hg. The starting materials set forth herein are either known or can be prepared in accordance with known methods.

The invention relates to hair styling and conditioning compositions, which are for use in heat styling hair, and which are dual phased in storage, and upon shaking or mixture becomes one-phased, and thereafter return to dual phase; wherein said composition comprises:

(a) a hydroalcoholic phase comprising at least one hair fixative; a salt which functions to break the emulsion made when the composition is shaken; and an emulsifier which functions to keep the fragrance solubilized in the hydro alcoholic phase; and (b) an anhydrous phase comprising a volatile silicone or a volatile hydrocarbon, or mixtures thereof.

More specifically, the compositions of the invention comprise:

(a) from about 50% to about 95% of a hydroalcoholic phase which comprises:
  (i) about 40% to about 90% of the total composition of water;
  (ii) about 0.1 to about 15%, of the total composition of monohydric alcohol; and
  (iii) about 0.01 to about 10.0%, or more preferably about 2 to about 5% of a hair fixative; and
  (iv) a salt
  (v) and an emulsifier;

(b) an anhydrous phase which comprises about 5% to about 50% of a volatile silicone or selected from the group consisting of dimethicone, cyclomethicone, and mixtures thereof, or a volatile hydrocarbon selected from the group consisting of isododecane, isohexadecane, and C13–C14 isoparaffin.

The hydroalcoholic phase is present at a most preferred range of about 65% to 85%.

The anhydrous phase is present at a most preferred range of about 35% to about 15%.

What follows now is a description of the ingredients which are included in the compositions of the invention.

Hydroalcoholic Phase

The hydroalcoholic phase of compositions of the invention comprises water and a monohydric alcohol.

Monohydric Alcohol

The monohydric alcohol that is used in compositions of the invention is a $C_1$ to $C_4$ monohydric alcohol. The monohydric alcohol is more preferably selected from the group consisting of ethanol, propanol, and butanol—most preferably ethanol.

A function of the monohydric alcohol in compositions of the invention is to solubilize the hair fixative in the hydroalcoholic phase.

Hair Fixative

The composition of the present invention comprises a hair fixative which can be a hair styling polymer for providing stylability to the hair. Hair styling polymers posses adhesive properties such that they are capable of shaping or styling the hair, and should be removable by shampooing or rinsing the hair. One or more hair styling polymers may be used. The total amount of hair styling polymer is generally from about 0.01% to about 10%, preferably from about 0.1% to about 5%, more preferably from about 2% to about 5%. A variety of hair styling polymers are suitable in the present invention. Particular polymers will be selected by the skilled artisan considering the solubility of the polymer in the composition and the ionicity of the composition Suitable hairstyling polymers are those which are soluble or dispersible (preferably micro dispersible) in the carrier described herein in the weight ratios employed in the composition.

Hair styling polymers include silicone-containing hair styling copolymers such as graft and block copolymers of silicone with a non-silicone adhesive polymer; sulfur-linked silicone containing copolymers; and non-silicone-containing hair styling polymers.

Non-silicone-containing hairstyling polymers include nonionic, anionic, cationic, and amphoteric polymers, and mixtures thereof. When used, the non-silicone-containing hair styling polymers are preferably present in a combined amount of from about 0.01% to about 10%, more preferably from about 0.1% to about 5% by weight of composition.

Suitable cationic polymers include Polyquaternium-4 (Celquat H-100; L200—supplier National Starch); Polyquaternium-11 (Gafquat 734; 755N—supplier ISP); Polyquaternium-16 (Luviquat FC370; FC550; FC905; HM-552 supplier by BASF); PVP/Dimethylaminoethyl methacrylate (Copolymer 845; 937; 958—ISP supplier); Vinyl Caprolactam/PVP/Dimethylaminoethyl Methacrylate copolymer (Gaffix VC-713; H2 OLD EP-1—supplier ISP); Chitosan (Kytamer L; Kytamer PC—supplier Amerchol); Polyquaternium-18 (Mirapol AZ-1 supplied by Rhone-Poulenc); Polyquaternium-24 (Quatrisoft Polymer LM-200—supplier Amerchol); Polyquaternium-28 (Gafquat HS-100 —supplier ISP) Polyquaternium-46 (Luviquat Hold—supplier BASF); and Chitosan Glycolate (Hadagen CMF; CMFP—supplier Henkel).

Preferred cationic polymers are Polyquaternium-4; Polyquaternium-11; Polyquaternium-16; PVP/Dimethylaminoethylmethacrylate; Vinyl Caprolactam/PVP/Dimethylaminoethyl Methacrylate copolymer; and Chitosan.

Suitable amphoteric polymers include Octylacrylmide/Acrylates/Butylaminoethyl Methacrylate Copolymer (Amphomer 28-4910, Amphomer LV-71 28-4971, Lovocryl-47 28-4947—National Starch supplier), and Methacryloyl ethyl betaine/methacrylates copolymer (Diaformer series supplier Mitsubishi). Preferred are Octylacrylmide/Acrylates/Butylaminoethyl Methacrylate Copolymer.

Useful nonionic polymers include PVP or Polyvinylpyrrolidone (PVP K-15,K-30, K-60, K-90, K-120—supplier ISP) (Luviskol K series 12, 17, 30, 60, 80, & 90—supplier BASF); PVP/VA (PVP/VA series S-630; 735, 635, 535, 335, 235—supplier ISP) (Luviskol VA); PVP/DMAPA acrylates copolymer (Styleze CC-10—supplier ISP); PVP/VA/Vinyl Propionate copolymer (Luviskol VAP 343 E, VAP 343 l, VAP 343 PM—supplier BASF); Hydroxylethyl Cellulose (Cellosize HEC—supplier BASF); and Hydroxylethyl Cellulose (Cellosize HEC—supplier Amerchol).

Preferred nonionic polymers are PVP or Polyvinylpyrrolidone and PVP/VA.

Anionic polymers suitable for use herein include VA/Crotonates/vinyl Neodecanonate Copolymer (Resyn 28-2930—National Starch supplier); Butyl Ester of PVM/MA (Gantrez A-425; ES-425; ES-435—supplier ISP); Ethyl Ester of PVM/MA (Gantrez ES-225; SP-215—supplier ISP); Acrylates/acrylamide copolymer (Lumiver 100P; Lumiver Low VOC, supplier BASF); Methacrylate Copolymer (Balance 0/55—National Starch supplier); Vinyl Acetate/Crotonic Acid copolymer (Luviset CA 66—supplier BASF); Isopropoyl Ester of PVM/MA Copolymer (Gantrez ES-335—supplier ISP); Acrylates Copolymer; Methacrylates/acrylates copolymer/amine salt (Diahold polymers—supplier Mitsubishi); 2-Butenedioic Acid (Z)—, Monoethyl Ester, Polymer with Methoxyethene (Omnirez 2000); VA/Butyl maleate/lsobonyl Acylate (Advantage Plusterpolymer—supplier ISP); Acrylates Copolymer (Amerhold DR-25—supplier Amerchol); Acrylates/Hydroxyesteracrylates Copolymer (Acudyne 225 supplier Rohm & Haas); Vinyl Acetate/Crotonic Acid/Vinyl Propionate copolymer (Luviset CAP—supplier BASF); PVP/Acrylates copolymer (Luviflex VBM 35—supplier BASF); Diglycol/CHDM/Isophthalates/SIP Copolymer (Eastman AQ 48, AQ 55—supplier Eastman Chemicals); Acrylates; Octacrylamide Copolymer (Versatyl-42 or Amphomer HC—National Starch supplier); TBA/AS copolymer (75/25—Mitsubishi Chemical Corp); and Carbomer (supplier B.F. Goodrich);.

Preferred anionic polymers are VA/Crotonates/Vinyl Neodecanonate Copolymer; Butyl Ester of PVM/MA; and Ethyl Ester of PVM/MA.

Salt

The hydroalcoholic phase of compositions of the invention also comprises an agent, such as an electrolyte, which serves to break the emulsion that is formed after the composition has been shaken or stirred. The electrolyte can be a salt such a sodium chloride.

Solubilizers or Emulsifiers

The compositions of the invention also comprise an emulsifier or a solubilizer which serves to solubilize oils in water. In compositions of the invention this solubilizer serves to solubilize fragrances in the hydroalcoholic phase. The hydrophilic-lipophilic (HLB) balance of emulsifiers which are employed in compositions of the invention can range from about 15 to about 20, but is not necessarily limited to that range. Nonlimiting examples of emulsifiers which may be used in compositions of the invention include: PEG 600 dilaurate, triethanolamine oleate, polyoxyethylene (10) stearyl ether and polyoxyethylene (4)sorbitan monolaurate. A most preferred emulsifier is PEG-2 Cocomonium Chloride.

Plasticizers

The compositions hereof may contain a plasticizer for the hair styling polymer. Any plasticizer suitable for use in hair care products or for topical application to the hair or skin can be used. A wide variety of plasticizers are known in the art. These include glycerine, diisobutyl adipate, butyl stearate, propylene glycol, diethylene glycol, other glycols, tri-$C_2$-$C_8$ alkyl citrates, including triethyl citrate and analogs of triethyl citrate.

Plasticizers are typically used at levels of from about 0.01% to about 200% preferably from about 0.05% to about 100%, more preferably from about 0.1% to about 50% by weight of the polymer.

Anhydrous Phase

The anhydrous phase of compositions of the invention comprise a volatile silicone, a volatile hydrocarbon and mixtures thereof. The volatile silicone, a volatile hydrocarbon or mixtures thereof can readily dissipate from the hair without residue and thereby, without weighing down the hair. The volatile silicone, a volatile hydrocarbon or mixtures thereof have conditioning properties.

The volatile silicone may be either a cyclic or linear polydiorganosiloxane. Preferably, the polydiorganosiloxane is a polydimethylsiloxane.

The number of silicone atoms in the cyclic silicones is preferably 3 to 7, most preferably 4 or 5.

Viscosities of these materials are generally less than 10 centipoise at 25° C.

Linear polydimethylsiloxanes useful in the invention generally have viscosities of less than about 5 centipoise at 25° C. The linear volatile silicones contain preferably from about 3 to about 9 silicon atoms and have the general formula:

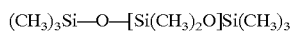

$(CH_3)_3Si-O-[Si(CH_3)_2O]Si(CH_3)_3$ wherein n=1–7.

Silicones of the above described types are widely available, for example, from Dow Corning as 244, 245, 344, 345 and 200 fluids (cyclopolymethylsiloxane blends), 200/5 fluid (a very short linear polydimethylsiloxane).

The volatile hydrocarbon may be a branched chain aliphatic hydrocarbon with about 6 to about 40 carbon atoms, preferably about 6 to about 20 carbon atoms. The volatile hydrocarbons are "nonpolar" which means that they have a solubility parameter of less than about $7.5 \, (cal/cm^3)^{0.5}$, most typically about $5.0 \, (cal/cm^3)^{0.5}$ to about $7.5 \, (cal/cm^3)^{0.5}$. The hydrocarbons preferably contain only carbon and hydrogen, and can have a cyclic, branched and/or chain configuration. Moreover, they can be saturated or unsaturated, preferably saturated. The hydrocarbons can be a mixture of two or more branched chained hydrocarbons and have different molecular weights. Nonlimiting examples of such hydrocarbons include isoparaffins from Exxon (Baytown, Tex.) called Isopar M (C13–C14 Isoparaffin) and Isopar C (C7–C8 Isoparaffin). Permethyl 99A (C12 isododecane), and petroleum distallates such as Soltrol 130, Soltrol 150 and Soltrol 170 from Phillips Chemical.

Optional Ingredients

Compositions of the invention may optionally include acids, bases, pH adjusters, fragrances, colorants, viscosity modifiers, preservatives, and anti-oxidants.

Compositions of the invention can take the form of leave-in liquids which can either be sprayed or poured onto hair.

Compositions of the invention are mixed or stirred or shaken so that the dual phases form one esthetically pleasing phase. Then compositions of the invention are typically worked into the hair (often wet hair) with the fingers or with a brush. Then a heating appliance such as a blow dryer or a curling iron, is applied to the hair while the hair is being styled as by combing. When compositions of the invention are applied in this manner the hair is styled as well as conditioned.

Composition which remains in a container which has been shaken will stay as one phase for one hour or more after which time it will separate out again into esthetically pleasing looking compositions which are dual-phased.

Compositions of the invention may be made either by preparing the hydroalcoholic phase and the anhydrous phase by conventional means, transferring the hydroalcoholic phase into a container, and then transferring the anhydrous phase into the container on top of the hydroalcoholic phase. Alternately, the aqueous and the hydroalcoholic phase can be mixed together and transferred into a container and the resulting one phase composition will separate into a dual-phased composition after on or more hours upon standing.

More specifically, compositions of the invention can be made by the following steps:
1. Add deionized water to a beaker or tank;
2. Add a salt, a liquid, citric acid and a UV absorber to said beaker or tank;
3. Add polymers and alcohol and mix until uniform;
4. Premix the fragrance and solubilizers until the resulting mixture is uniform, and then add this mixture to said beaker or tank;
5. Add preservative and dissolved dyes into said beaker or tank and mix until uniform;
6. Add volatile silicone or hydrocarbon to said beaker or tank and continue mixing during filling process into a container.

The following are compositions of the invention which have been made. These compositions were made by methods which are conventional in the art.

EXAMPLE 1

| Ingredient/Description | Wt. % |
| --- | --- |
| Water, Soft | 68.57 |
| Liquid Citric Acid, 50% Active | 0.09 |
| Sodium Chloride | 0.09 |
| PVP/VA E-635 | 4.00 |
| SD Alcohol 40-B (190 Proof) | 8.00 |
| Gafquat 734 ® | 3.00 |
| Benzephenone-4 | 0.05 |
| DMDM Hydantoin & Iodopropynyl Butylcarbamate | 0.2 |
| PEG-2 Cocomonium Chloride | 0.80 |
| Fragrance | 0.20 |
| Cyclopentasiloxane | 15.00 |

EXAMPLE 2

| Ingredient/Description | Wt. % |
| --- | --- |
| Water, Soft | 77.86 |
| Sodium Chloride | 0.09 |
| Amaze ®(National Starch) | 1.50 |
| PVP/VA E-635 | 5.00 |
| SD Alcohol 40-B (190 Proof) | 2.00 |
| Benzephenone-4 | 0.05 |
| DMDM Hydantoin & Iodopropynyl Butylcarbamate | 0.2 |
| Isoceteth-20 | 0.15 |
| Oleth-20 | 0.52 |
| Fragrance | 0.13 |
| Cyclopentasiloxane | 12.50 |

EXAMPLE 3

| Ingredient/Description | Wt. % |
| --- | --- |
| Water, Soft | 69.33164 |
| Liquid Citric Acid, 50% Active | 0.15000 |
| PVP/VA E-635, 50% Active | 4.00000 |
| SD Alcohol 40-B (190 Proof) | 8.00000 |
| Gafquat 734 ® | 3.00000 |
| Merguard 1190 ® | 0.04000 |
| DMDM Hydantoin | 0.09000 |

-continued

| Ingredient/Description | Wt. % |
|---|---|
| PEG-2 Oleamonium Chloride & Propylene GL | 0.26000 |
| Fragrance | 0.12800 |
| Cyclopentasiloxane | 15.00000 |

The above examples illustrate the invention, but are not meant to limit it.

Beneficial Properties of Compositions of the Invention

Compositions of the invention have been shown to lower the wet combing force of treated, bleached and waved 2 g hair tresses, using Instron 5500 series measurements carried out in a manner known to the art. Wet hair which has instrumentally measured low wet combing force, is perceived by consumers as better conditioned hair.

Compositions of the invention provide leave-in compositions which can be applied to hair (as a spray or as a liquid), are then worked into the hair with the fingers or with an appliance such as a comb or a brush. Then the hair can be heat styled with a heating appliance such as a blow drier or a curling iron.

The resulting heat styled hair unexpectedly has more conditioned properties, is softer, and has more body. It was unexpected that a dual-phased product which had a hydroalcoholic phase containing a hair fixative and an anhydrous phase containing a volatile silicone hair conditioning agent would be a composition that simultaneously provided styling benefits and conditioning benefits to heat styled hair. Salon blitz testing showed that compositions of the invention provide significantly more body, and bounce to the hair while leaving hair less limp and flat in appearance.

What is claimed is:

1. A hairstyling and conditioning composition which comprises:
   (a) from about 50% to about 95% of the total composition of a hydroalcoholic phase comprising:
      (i) about 40% to about 90% of the total composition of water;
      (ii) about 0.1 to about 15% of the total composition of $C_1$ to $C_4$ monohydric alcohol; and
      (iii) about 0.01 to about 10% of the total composition of a hair fixative styling polymer;
      (iv) a salt; and
   (b) an (v) an emulsifier anhydrous phase comprising about 5% to about 50% of a volatile silicone or a volatile hydrocarbon with 6 to 40 carbon atoms, or mixtures thereof; and wherein the composition is dual phase until agitated, becomes single phase upon agitation, and then returns to dual phase after agitation.

2. A composition in accordance with claim 1, wherein said composition returns to dual phase one or more hours after agitation.

3. A composition according to claim 1, wherein said hydroalcoholic phase is present at about 65% to about 85%.

4. A composition in accordance with claim 1, wherein said anhydrous phase is present at about 35% to about 15%.

5. A composition according to claim 1, wherein said hydroalcoholic phase comprises the monohydric alcohol which is ethanol.

6. A composition according to claim 1, wherein said fixative styling polymer is selected from the group consisting of Polyquaternium-4, Polyquaternium-11, Polyquaternium-16, PVP/Dimethylamino ethyl methacrylate, Vinyl Caprolactam/PVP/Dimethylaminoethyl Methacrylate copolymer, Polyquaternium-18, Polyquaternium-24, Polyquaternium-28, Polyquaternium-46, Chitosan Glycolate, Octylacrylamide/Acrylates/Butylaminoethyl Methacrylate Copolymer, Methacryloyl ethyl betaine/methacrylates copolymer, Polyvinylpyrrolidone, PVP/VA, PVP/DMAPA acrylates copolymer, PVP/VA/Vinyl Propionate copolymer, VA/Crotonates/Vinyl Neodecanonate Copolymer, Butyl Ester of PVM/ MA, Ethyl Ester of PVM/MA, Acrylates/acrylamide copolymer, Methacrylate Copolymer, Vinyl Acetate/Crotonic Acid copolymer, Isopropyl Ester of PVM/MA Copolymer, Acrylates Copolymer; Methacrylates/acrylates copolymedamine salt, 2-Butenedioic Acid (Z)-Monoethyl Ester, VA/Butyl maleate/Isobornyl Acylate, Acrylates!Hydroxyesteracrylates Copolymer, Vinyl Acetate/Crotonic/Acid/Vinyl Propionate copolymer, PVP/Acrylates Copolymer, Diglycol/CHDN/Isopthalates/CIP Copolymer, Octacrylamide Copolymer, TBA/AS Copolymer and mixtures thereof.

7. A method for heat styling hair which comprises:
   (a) applying to said hair a composition according to claim 1; and then
   (b) applying to said hair, heat from a heating appliance.

* * * * *